(12) United States Patent
Georgeson et al.

(10) Patent No.: US 10,416,103 B2
(45) Date of Patent: Sep. 17, 2019

(54) THERMO-CHROMATIC WITNESS FEATURES FOR LIGHTNING STRIKE INDICATION IN BOTH METALLIC AND COMPOSITE STRUCTURES

(71) Applicant: The Boeing Company, Chicago, IL (US)

(72) Inventors: Gary Georgeson, Tacoma, WA (US); Jeong-Beom Ihn, Bellevue, WA (US)

(73) Assignee: THE BOEING COMPANY, Chicago, IL (US)

( * ) Notice: Subject to any disclaimer, the term of this patent is extended or adjusted under 35 U.S.C. 154(b) by 501 days.

(21) Appl. No.: 15/143,958

(22) Filed: May 2, 2016

(65) Prior Publication Data

US 2017/0315072 A1  Nov. 2, 2017

(51) Int. Cl.
| | | |
|---|---|---|
| *G01N 25/72* | (2006.01) | |
| *G01N 21/64* | (2006.01) | |
| *B64D 45/02* | (2006.01) | |
| *G01K 11/12* | (2006.01) | |
| *B64D 45/00* | (2006.01) | |

(52) U.S. Cl.
CPC ............ *G01N 25/72* (2013.01); *B64D 45/02* (2013.01); *G01N 21/64* (2013.01); *B64D 2045/0085* (2013.01); *G01K 11/12* (2013.01); *G01N 2201/101* (2013.01)

(58) Field of Classification Search
CPC .. G01N 25/72; G01N 21/64; G01N 2201/101; B64D 45/02; B64D 2045/0085; G01K 11/12
USPC ......................................................... 250/365
See application file for complete search history.

(56) References Cited

U.S. PATENT DOCUMENTS

| | | | |
|---|---|---|---|
| 9,346,559 B1 | 5/2016 | Skelton | |
| 2010/0029140 A1* | 2/2010 | O'Rourke | H01R 13/6392 439/668 |
| 2014/0045366 A1* | 2/2014 | O'Rourke | H01R 31/02 439/488 |
| 2014/0273240 A1* | 9/2014 | Georgeson | G01N 31/229 436/7 |
| 2015/0004831 A1* | 1/2015 | O'Rourke | H01R 31/02 439/488 |
| 2017/0005443 A1* | 1/2017 | O'Rourke | H01R 31/02 |

FOREIGN PATENT DOCUMENTS

| | | |
|---|---|---|
| CN | 102618254 B | 12/2014 |
| EP | 2778661 A2 | 9/2014 |

OTHER PUBLICATIONS

Patent Office of the Cooperation Council for the Arab States of HTE Gulf; Examination Report; GC Patent Appliation Serial No. GC 2017-33310; dated Mar. 31, 2019.

* cited by examiner

*Primary Examiner* — David P Porta
*Assistant Examiner* — Gisselle M Gutierrez
(74) *Attorney, Agent, or Firm* — Parsons Behle & Latimer (57) ABSTRACT

A system includes a structure and a material applied to a portion of the structure. The material may be adapted to change color locally in response to localized heating of the portion of the structure to a first threshold temperature due to an electrical current within the structure. The system may further include a detector configured to receive light from the structure to enable detection of a pathway of the electrical current through the structure based on a position of the color.

20 Claims, 7 Drawing Sheets

THERMO-CHROMATIC WITNESS FEATURES FOR LIGHTNING STRIKE INDICATION IN BOTH METALLIC AND COMPOSITE STRUCTURES

FIELD OF THE DISCLOSURE

This disclosure is generally related to thermo-chromatic witness features for lightning strike indication in both metallic and composite structures.

BACKGROUND

With the increasing use of carbon fiber reinforced polymer (CFRP) composite structures in the aerospace and commercial aircraft industry, there is an increasing need for the advancement of efficient non-destructive evaluation (NDE) methods for the detection of composite damage. An especially dangerous form of damage results from lightning strike, which can induce thermal damage that is difficult to detect.

Typical inspection methods for thermal damage due to lightning strikes may include using ultrasonic instrumentation to determine whether damage, such as delamination, separation, and/or cracking, has occurred. Another method of inspection includes performing a Fourier transform infrared (FTIR) analysis of a spectral signal taken from the aircraft to correlate a visual inspection to heat damage for specific resin coatings. However, these methods are time consuming and may be inaccurate.

Other methods for detecting damage due to lightning strikes may involve determining a position of an initial strike point based on marks, discoloration, or damage caused by the initial lightning strike, and inspecting each component of the aircraft in proximity to the initial strike point. However, many of the components inspected may fall outside of a particular pathway followed by the electrical current from the lightning strike and are therefore unlikely to have been damaged. Because it is unknown which pathway the current may have taken, these components may be needlessly inspected. The inspections may also include time-consuming, expensive, and/or invasive dismantling processes. What is needed is a quick, reliable, and non-invasive method for determining a pathway taken by current from a lightning strike through a structure, and for determining the extent to which components along the pathway may have been damaged.

SUMMARY

In an embodiment, a system includes a structure and a thermo-chromatic material applied to the structure. The thermo-chromatic material is adapted to change to a color locally in response to localized heating of the structure. The heating may be caused by an electrical current from a lightning strike. By examining the position and extent of the color change, an estimation of damage to the structure due to the lightning strike may be determined.

In an embodiment, a method includes changing a material applied to a portion of a structure to a first color in response to heating of the portion of the structure to a first threshold temperature due to an electrical current within the structure. The method further includes detecting a pathway of the electrical current through the structure based on a position of the first color.

In some embodiments, the method also includes estimating, based at least on the first color, an extent of damage produced by the electrical current along the detected pathway of the electrical current through the structure. In some embodiments, the method includes changing a material applied to a second portion of the structure to a second color distinct from the first color in response to heating of the second portion of the structure to a second threshold temperature greater than the first threshold temperature. In some embodiments, the method includes successively changing additional materials applied to additional portions of the structure to additional colors distinct from the first color and distinct from each other in response to heating of the additional portions of the structure to additional successively increasing threshold. In some embodiments, the method includes estimating, based at least on the first color and the additional colors, an extent of damage produced by the electrical current along the detected pathway of the electrical current through the structure.

In some embodiments, the method includes scanning a surface of the structure with a detector. The method further includes receiving, at the detector, light from the structure. The method also includes locating the position of the first color based on the light from the structure. In some embodiments, the method includes directing a light source at the structure during the scanning. The light source may be an ultraviolet light source and the first color may be substantially invisible under non-ultraviolet light. In some embodiments, the first threshold temperature is between 200° C. and 300° C.

In an embodiment, a system includes a structure and a first material applied to a portion of the structure. The material is adapted to change to a first color locally in response to localized heating of the portion of the structure to a first threshold temperature due to an electrical current within the structure. The system further includes a detector configured to receive light from the structure to enable detection of a pathway of the electrical current through the structure based on a position of the first color.

In some embodiments, the first color enables estimating an extent of damage produced by the electrical current along the pathway of the electrical current through the structure. In some embodiments, the system further includes a second material applied to a second portion of the structure. The second material is adapted to change to a second color, distinct from the first color, in response to heating of the portion of the structure to a second threshold temperature greater than the first threshold temperature. In some embodiments, the system also includes additional materials applied to additional portions of the structure. The additional materials are adapted to change to additional colors, distinct from the first color and distinct from each other, in response to heating of the additional portions of the structure to additional successively increasing threshold temperatures. In some embodiments, the first color and the additional colors enable estimating an extent of damage produced by the electrical current along the detected pathway of the electrical current through the structure.

In some embodiments, the system also includes a light source directed toward the structure. The light source may be an ultraviolet light source and the first color may be substantially invisible under non-ultraviolet light.

In some embodiments, the structure includes a copper foil applied to a composite aircraft, a conductive mesh of a composite aircraft, a dielectric top of a composite aircraft, a lightning diversion strip, a grounding cable or plate, a portion of a lightning protection layer of an aircraft, or any combination thereof. In some embodiments, the material includes a thermo-chromatic witness material.

In an embodiment, a method includes applying a first material to a first portion of a structure. The first material is adapted to change to a first color in response to heating of the first portion of the structure to a first threshold temperature due to an electrical current within the structure. The method further includes applying a second material to a second portion of the structure. The second material is adapted to change to a second color, distinct from the first color, in response to heating of the second portion of the structure to a second threshold temperature.

In some embodiments, the first material is incorporated into a first set of applique strips and the second material is incorporated into a second set of applique strips. The first set of applique strips and the second set of applique strips are applied to the structure in a repeating pattern. In some embodiments, the first material is incorporated into a first portion of a coating matrix and the second material is incorporated into a second portion of coating matrix. The coating matrix is applied to the structure. In some embodiments, the first material is incorporated into a first portion of a resin of a lightning protection layer and the second material is incorporated into a second portion of the resin of the lightning protection layer.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the disclosure as defined by the appended claims.

DETAILED DESCRIPTION

Figure 1:
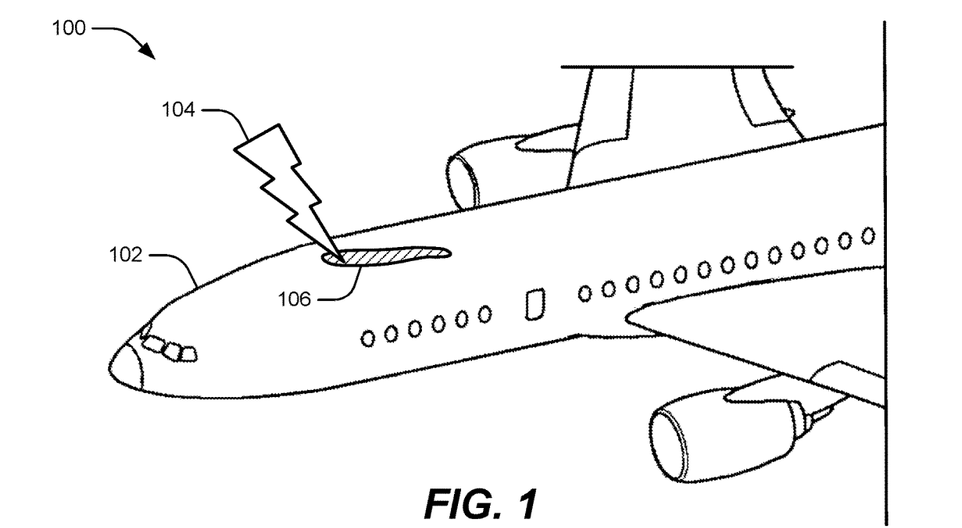
FIG. 1 depicts an embodiment of an aircraft 100 with a thermo-chromatic material.

Referring to FIG. 1, an embodiment of an aircraft 100 is depicted. The aircraft 100 may include composite materials, metallic materials, other types of building materials, or combinations thereof. A surface 102 of the aircraft 100 may include a thermo-chromatic witness material applied thereto as described herein. At some time during the operations of the aircraft 100, the surface 102 of the aircraft 100 may get struck by lightning 104. In response to heat generated within the structure of the aircraft 100, the thermo-chromatic witness material may change color creating a color changed region 106 of the surface 102. Because the color changed region 106 is formed due to heat generated by electrical current from the lightning 104, the color changed region 106 may substantially follow the pathway of the electrical current until the electrical current leaves the surface 102 of the aircraft 100 or dissipates such that it no longer generates sufficient heat to activate the thermo-chromatic witness material. In some embodiments, the thermo-chromatic material is selected such that the color changed region 106 may be visible under ultraviolet light and may be substantially invisible under non-ultraviolet light.

An advantage of applying the thermo-chromatic witness material to the surface 102 of the aircraft is that it enables detection of both the strike point of the lightning 104 and the pathway taken by the electrical current through the surface 102 of the aircraft 100. By locating the position of the color changed region 106, a more accurate estimation may be made of which components may have been damaged due to the lightning 104. Thus, time and expense may be saved by inspecting only those components proximate to the color changed region 106, as those components are more likely to have been overheated or otherwise damages by the electrical current. Other benefits and advantages associated with the embodiment of FIG. 1 may be apparent to persons of ordinary skill in the relevant art having the benefit of this disclosure.

Figure 2:
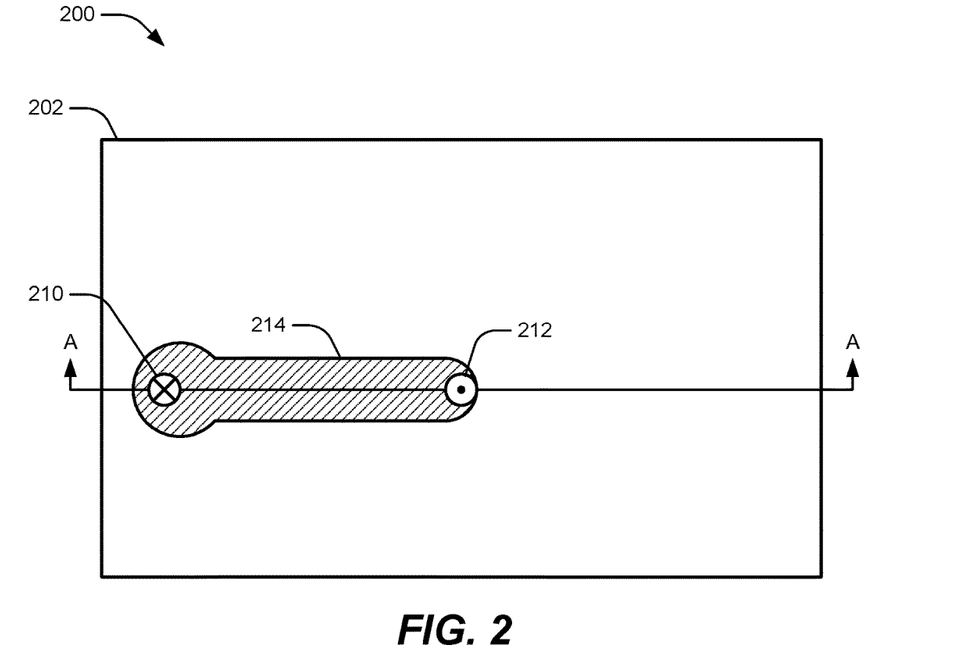
FIG. 2 depicts an embodiment of a system for lightning strike indication.
Figure 2A:
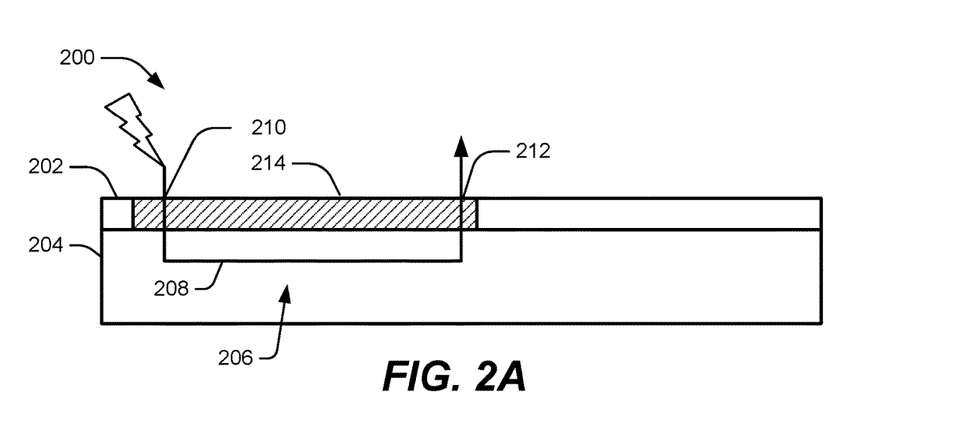
FIG. 2A depicts a cross-section view of the embodiment of the system for lightning strike indication.

Referring to FIGS. 2 and 2A, an embodiment of a system 200 for lightning strike indication is depicted. FIG. 2 depicts a top view of the system 200. FIG. 2A depicts a cross-section view of the system 200 along the cross-section line designated by the symbol A of FIG. 2. The system 200 may include a thermo-chromatic witness material 202 applied to a structure 204.

The thermo-chromatic witness material 202 may include any substance that changes color due to a change in temperature. For lightning detection applications, the color change may be sufficiently permanent to remain changed until inspection of the system 200 may take place. In some embodiments, the thermo-chromatic witness material 202 may change color or fluoresce at a threshold temperature between 200° C. and 300° C.

Different types of thermo-chromatic witness materials may be associated with different time intervals during which heat is applied in order to activate. In some embodiments, in order to detect lightning strikes, the thermo-chromatic witness material 202 is activated during the short time interval associated with a lightning strike. For example, the thermo-chromatic witness material 202 may activate within a time period between 0.1 second and 1 second. Further, the thermo-chromatic witness material 202 may retain its changed color for a sufficient time interval to enable inspection of the system 200. For example the thermo-chromatic witness material may retain its changed color for up to several days or longer.

The structure 204 may include any structure for which lightning strike protection may be desirable. In some embodiments, the structure 204 may be a portion of an aircraft. For example, the structure 204 may include a copper foil applied to a composite aircraft, a conductive mesh of a composite aircraft, a dielectric top of a composite aircraft, a lightning diversion strip, a grounding cable or plate, a portion of a lightning protection layer of an aircraft, another portion of an aircraft, or combinations thereof.

At some time during operation, the system 200 may be struck by lightning. The lightning may generate an electrical current that enters the structure 204 at an entrance point 210. The current may travel through the structure 204 along a pathway 208 before exiting through an exit point 212. In some embodiments, the electrical current may dissipate, either partially or entirely, along the pathway 208. For example, the structure 204 may be designed to redirect and/or spread the electrical current over a large area resulting in a reduction of the electrical current. In some instances, the electrical current may be completely dissipated before reaching the exit point 212.

As the electrical current moves through the structure 204 along the pathway 208, a portion 206 of the structure 204 in proximity to the pathway may become heated. When the portion 206 reaches a threshold temperature, the thermo-chromatic witness material 202 applied at the portion 206 may change to another color, forming a color changed region 214. The hatching shown in FIGS. 2 and 2A indicate that a color of the color changed region 214 differs from the rest of the thermo-chromatic witness material 202.

An advantage of the system 200 is that by forming a color change region 214 in the thermo-chromatic witness material 202, the system 200 provides a quick, reliable, and non-invasive method for determining a pathway taken by current from the lightning strike through the structure 204, and for determining the extent to which components along the pathway 208 may have been damaged. Other benefits and advantages of the system 200 may be apparent to persons of ordinary skill in the relevant art having the benefit of this disclosure.

Figure 3:
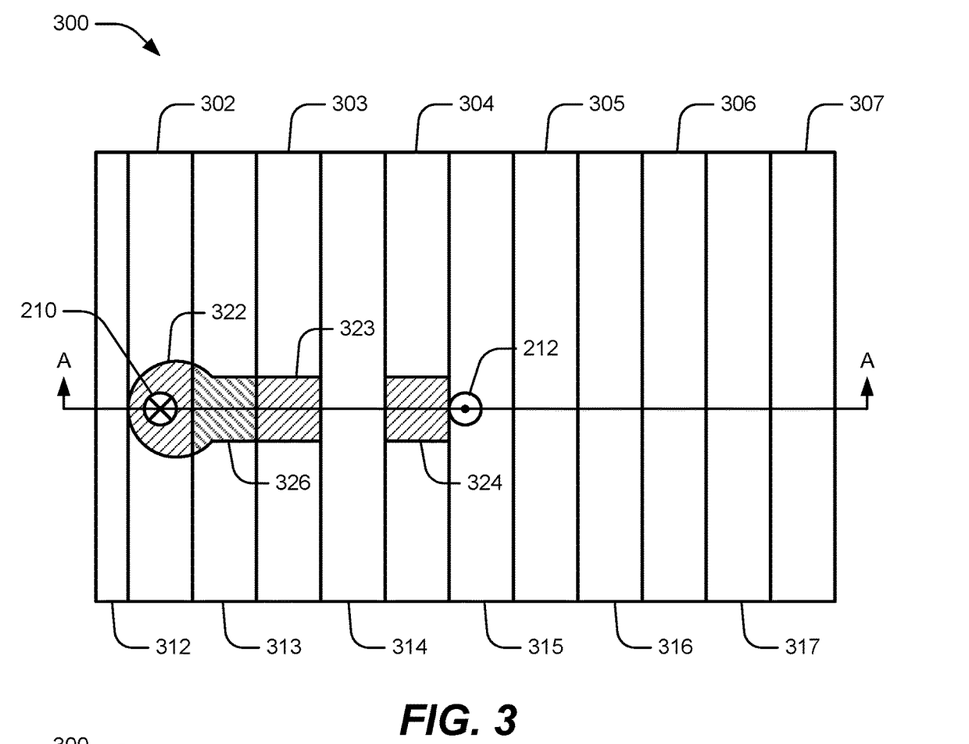
FIG. 3 depicts an embodiment of a system for lightning strike indication.
Figure 3A:
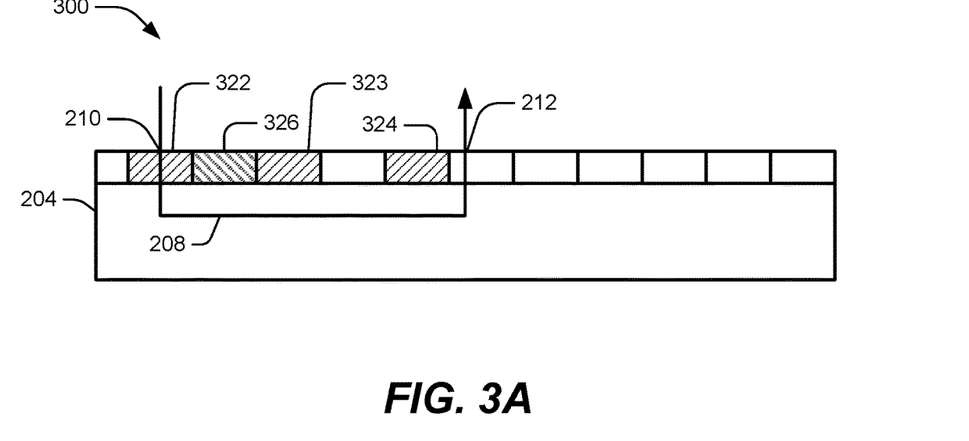
FIG. 3A depicts a cross-section view of the embodiment of the system for lightning strike indication.

Referring to FIGS. 3 and 3A, an embodiment of a system 300 for lightning strike indication is depicted. The system 300 may include a first set of applique strips 302-307 and a second set of applique strips 312-317. The first set of applique strips 302-307 may include a first thermo-chromatic witness material that changes color at a first threshold temperature. The second set of applique strips 312-317 may include a second thermo-chromatic witness material that changes color at a second threshold temperature that is greater than the first threshold temperature.

The electrical current passing through the structure 204 may be the most intense near the entrance point 210. As it travels along the pathway 208, it may lose power as it heats the structure 204 and/or dissipates through a large conductive area. As such, the structure 204 may be heated to higher temperatures along the pathway 208 near the entrance point 210 as compared to near the exit point 212.

As depicted in FIGS. 3 and 3A, the electrical current may heat portions of the structure 204 in contact with some of the applique strips (e.g., the applique strips 302-304) to a temperature beyond the first threshold temperature. In response to the heat, the first thermo-chromatic witness material included in the applique strips 302-304 may change color to form color changed regions 322-324 over the heated portions of the structure 204. Likewise, the current may heat other portions of the structure 204 in contact with other applique strips (e.g., the applique strips 313-315). Near the entrance point 210, the heat may exceed the second threshold temperature causing the second thermo-chromatic witness material included in the applique strip 313 to change color to form another color change region 326. As the pathway 208 moves away from the entrance point 210, the heat generated by the electrical current may decrease. As such, further from the entrance point 210, the heat may not exceed the second threshold temperature, resulting in the formation of no color change regions within some of the applique strips (e.g., the applique strips 314, 315) despite being in contact with heated portions of the structure 204.

By including a first thermo-chromatic witness material in some of the applique strips and including another thermo-chromatic witness material in other applique strips, a determination may be made of the extent of heating within the structure 204 at multiple portions of the structure 204 along the pathway 208. For example, a determination may be made that the portions of the structure 204 that are adjacent to the applique strips 302, 303, and 313 may have been subjected to more heating than the portions of the structure 204 adjacent to the applique strips 304, 314, 315 because the temperatures near the applique strip 313 exceeded the second threshold temperature while the temperatures near the applique strips 314, 315 did not exceed the second threshold temperature. Thus, components within the structure 204 near the applique strips 302, 303, 313 may have been subjected to more heat and consequently may be more likely to have been damaged by the lightning strike. Colors of the first thermo-chromatic witness material and the second thermo-chromatic witness material may be distinct from each other after their respective threshold temperatures are reached in order to enable a determination of temperature ranged reached at each portion of the structure 204.

As shown in FIG. 3, the applique strips 302-307 that include the first thermo-chromatic witness material and the applique strips 312-317 that include the second thermo-chromatic witness material may be alternately applied to produce an even heat sampling for both temperature thresholds across the structure 204. In some embodiments, more than two types of thermo-chromatic witness materials may be used. For example, additional applique strips including additional thermo-chromatic witness materials may be applied to additional portions of the structure 204. The additional thermo-chromatic witness materials may be successively adapted to change to additional colors in response to heating of the additional portions of the structure 204 to additional successively increasing threshold temperatures. The additional applique strips may be sequentially laid along the structure 204 to produce an even heat sampling for each temperature threshold. Further, each of the thermo-chromatic witness materials may change to colors distinct from each other. As such, a range of temperatures experienced by the structure 204 may be mapped.

An advantage associated with alternating between applique strips that include a first thermo-chromatic witness material and applique strips that include a second thermo-chromatic witness material is that the system 300 may provide a quick, reliable, and non-invasive method for determining the pathway 208 taken by current from a lightning strike through the structure 204, and for determining the extent to which components along the pathway 208 may have been damaged. Further, because the system 300 incorporates applique strips, it may be easily constructed. Other benefits and advantages of the system 300 may be apparent to persons of ordinary skill in the relevant art having the benefit of this disclosure.

Figure 4:
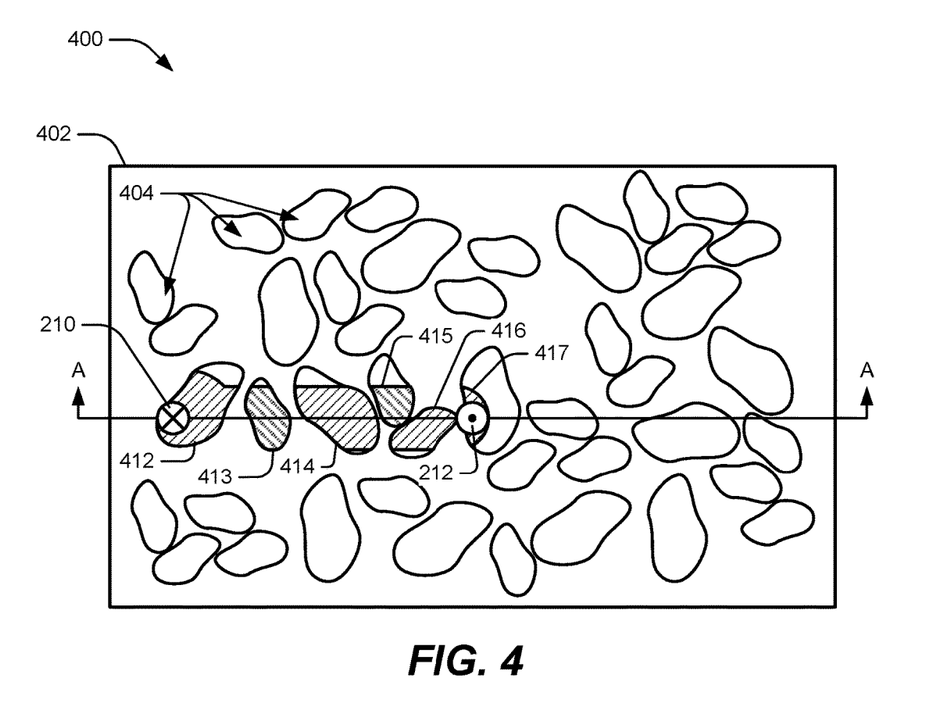
FIG. 4 depicts an embodiment of a system for lightning strike indication.
Figure 4A:
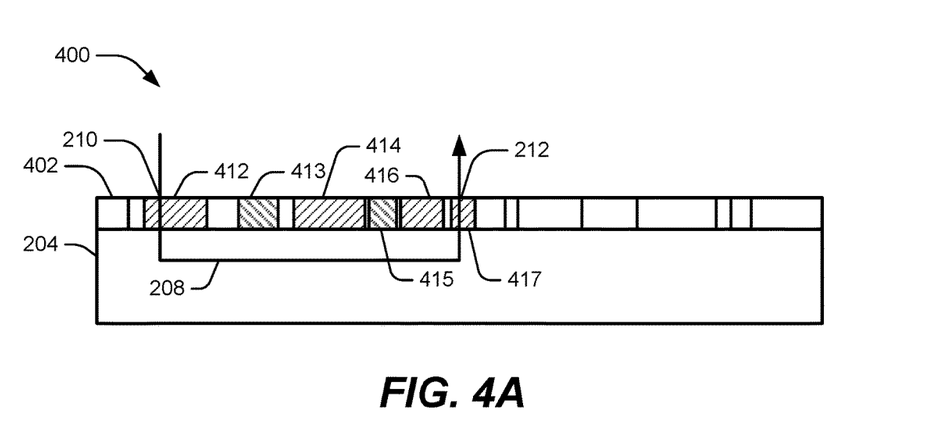
FIG. 4A depicts a cross-section view of the embodiment of the system for lightning strike indication.

Referring to FIGS. 4 and 4A, an embodiment of a system 400 for lightning strike indication is depicted. The system 400 may include a matrix material 402 applied to the structure 204 with multiple thermo-chromatic witness particles 404 incorporated therein.

In some embodiments, the matrix material 402 may include a resin or another type of coating applied to the structure 204. The matrix material 402 may be applied to the structure 204 by spraying, brushing, another type of application process, or combinations thereof. The thermo-chromatic witness particles 404 may be incorporated into the matrix material 402 before application of the matrix material 402 to the structure 204. Alternatively, in some embodiments, the thermo-chromatic witness particles 404 may be incorporated into the matrix material 402 after the application thereof.

Some of the thermo-chromatic witness particles 404 may include a first thermo-chromatic witness material and some of the thermo-chromatic witness particles 404 may include a second thermo-chromatic witness material. The first thermo-chromatic witness material may change to a first color when heated to a first threshold temperature and the second thermo-chromatic witness material may change to a second color, distinct from the first color, when heated to a second threshold temperature, different than the first threshold temperature. For example, upon heating due to the current along the pathway 208, some of the particles 404 may change to a first color forming color changed regions (e.g., the color changed regions 412, 414, 417) of the particles. Other color changed regions (e.g., the color changed regions 413, 415) may correspond to a second color distinct from the first.

In some embodiments, as depicted in FIGS. 4 and 4A, the particles 404 are mixed into the matrix material 402 haphazardly. Alternatively, in some embodiments, the first set of particles 412, 414, 416, 417 are incorporated into a first portion of the matrix material 402 and the second set of particles 413, 415 are incorporated into a second portion of the matrix material 402, with the first and second portions initially separated. Each portion of the matrix material 402 may then be applied to the structure 204 in a pattern. Although not depicted in FIG. 4, in some embodiments, some of the particles 404 include additional thermo-chromatic witness materials that change to additional colors, distinct from the first color and second color and distinct from each other, in response to heating of the additional portions of the structure 204 to additional successively increasing threshold.

As electrical current passes from the entrance point 210 to the exit point 212 along the pathway 208, it may heat the structure 204. If portions of the structure 204 are heated beyond the first threshold temperature, then the thermo-chromatic witness particles 404 may change color based on a temperature range associated with a respective thermo-chromatic witness particles material. The change in color may enable a determination of the position of potential damage to the structure 204 and/or the extent of damage. Other benefits and advantages of the system 400 may be apparent to persons of ordinary skill in the relevant art having the benefit of this disclosure.

Figure 5:
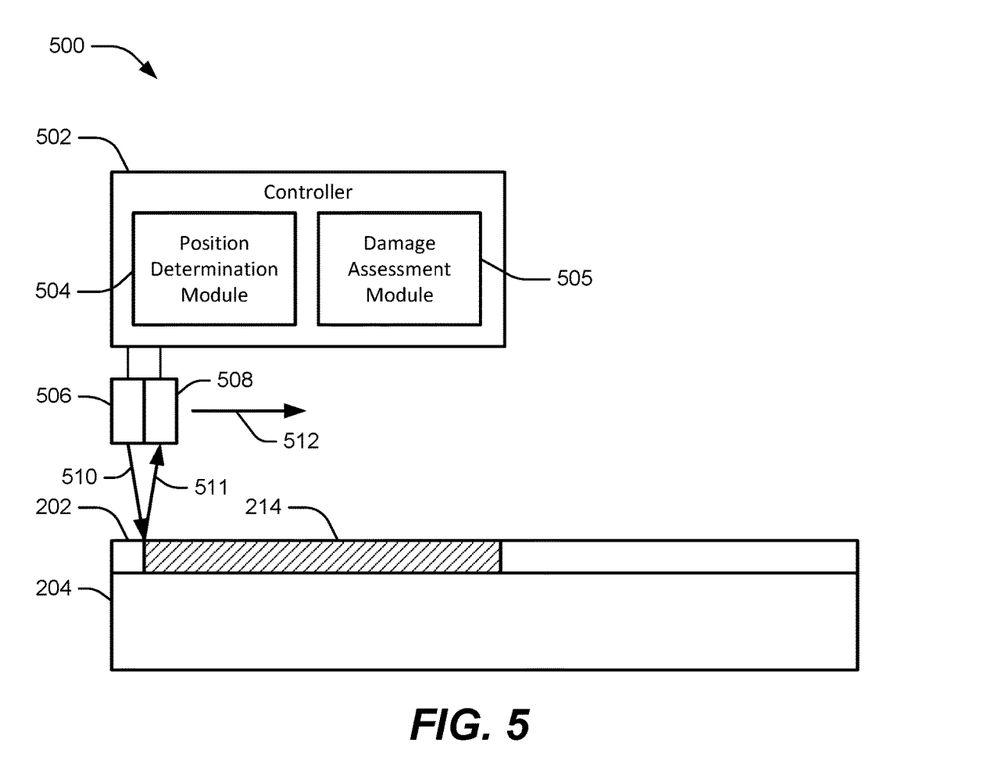
FIG. 5 depicts an embodiment of a system for detecting a position and the extent of potential damage due to lightning strikes.

Referring to FIG. 5, an embodiment of a system 500 for detecting a position and the extent of potential damage due to lightning strikes is depicted. The system 500 may include a controller 502, a light source 506, and a detector 508.

The controller 502 may perform control functions as described herein. In some embodiments, the controller is implemented using a processor and memory. For example, the processor may include a central processing unit (CPU), a graphical processing unit (GPU), a peripheral interface controller (PIC), another type of processing unit, or combinations thereof. In some embodiments, the controller is implemented using programmable or fixed circuit logic such as a field programmable gate array (FPGA), an application specific integrated circuit (ASIC), an integrated circuit (IC) device, another type of circuit logic, or combinations thereof.

The controller 502 may include a position determination module 504 that receives input from the detector 508. Based on the input, the position determination module 504 may determine a position of the color changed region 214. The controller 502 may further include a damage assessment module 505 that determines the extent of potential damage to the structure 204 at the position. In some embodiments, the controller may generate a visual depiction that maps the position and an estimate of the extent of potential damage to a three-dimensional model of the structure 204.

During operation, the light source 506 may be directed at the structure 204. In some embodiments, the light source 506 may include an ultraviolet light lamp. The light source 506 may emit light 510 (e.g. ultraviolet light) which may cause the thermo-chromatic witness material 202 to fluoresce. Reflected and/or additional light 511 showing the fluoresced thermo-chromatic witness material may be received at the detector 508. The detector may send image data based on the light 511 to the position determination module 504.

In order to determine position information, the controller 502 may control the detector 508 to scan a surface of the thermo-chromatic witness material 202. For example, the detector 508 may scan in the direction indicated by the arrow 512. Scanning may include rotational movements, translational movements, other types of movements, or combinations thereof. In order to effectuate the scanning, the controller 502 may include gears, motors, or other mechanical devices (not shown) to apply movement to the detector 508.

Based on the light from the structure 204, the controller 502 may locate the position of the color changed region 214. Further, the controller 505 may analyze the colors present at the color changed region 214 to determine the extent of heating of the structure 204 throughout each position of the structure 204 and thereby generate an estimate of damage that may have occurred at one or more components of the structure 204.

Figure 6:
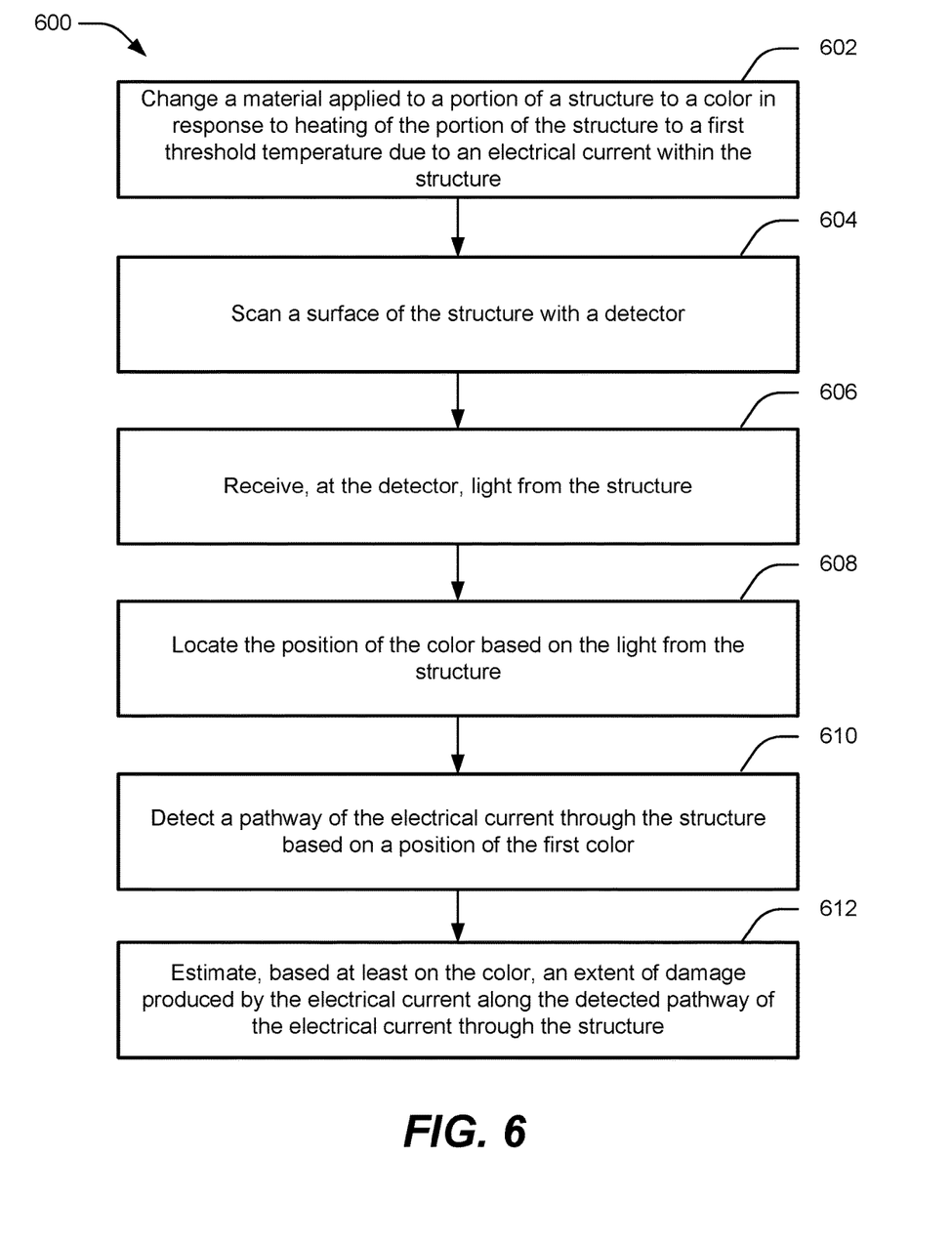
FIG. 6 is a flowchart that depicts an embodiment of a method for lightning strike indication.

Referring to FIG. 6 an embodiment of a method 600 for lightning strike indication is depicted. The method 600 may include changing a material applied to a portion of a structure to a color in response to heating of the portion of the structure to a first threshold temperature due to an electrical current within the structure, at 602. For example, the thermo-chromatic witness material 202 may change to the color represented by the hatching of FIG. 2 at the color changed region 214 in response to heating of the portion 206 of the structure 204 proximate to the electrical current path 208.

The method 600 may further include scanning a surface of the structure with a detector, at 604. For example, the surface of the structure 204 may be scanned by the detector 508.

The method 600 may also include receiving, at the detector, light from the structure, at 606. For example, the light 511 may be received at the detector 508.

The method 600 may include locating the position of the color based on the light from the structure receiving, at the detector, light from the structure, at 608. For example, the position of the color changed region 214 may be determined at the position determination module 504.

The method 600 may further include detecting a pathway of the electrical current through the structure based on a position of the first color, at 610. For example, the pathway 208 may be detected based on the pathway of the color changed region 214.

The method 600 may also include estimating, based at least on the color, an extent of damage produced by the electrical current along the detected pathway of the electrical current through the structure, at 612. For example, the damage assessment module 505 may determine an extent of damage along the color changed region 214 based on the color of the color changed region 214.

Figure 7:
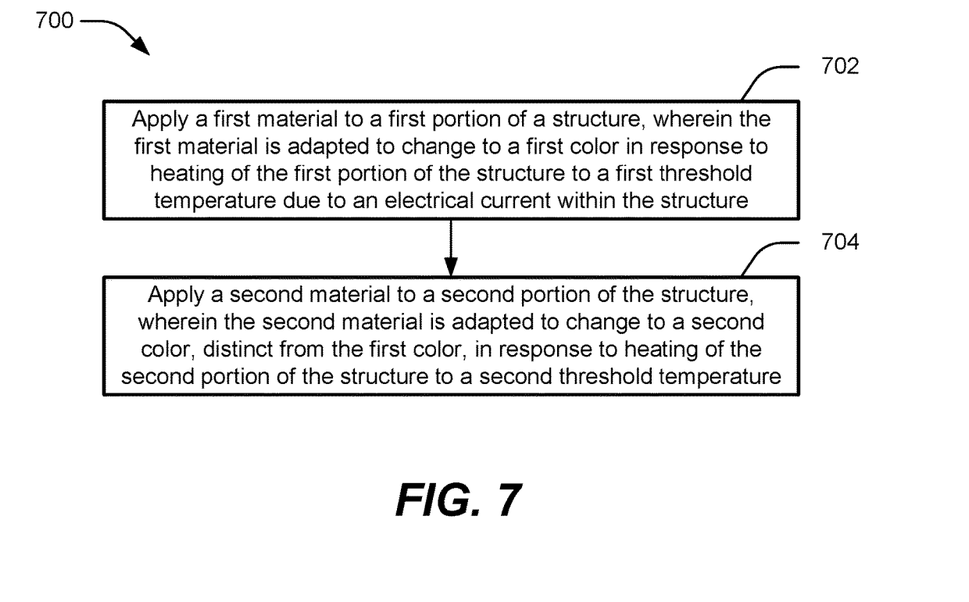
FIG. 7 is a flowchart that depicts an embodiment of a method for making a lightning strike indication system.

Referring to FIG. 7 an embodiment of a method 700 for making a lightning strike indication system is depicted. The method 700 may include applying a first material to a first portion of a structure, at 702. The first material may adapted to change to a first color in response to heating of the first portion of the structure to a first threshold temperature due to an electrical current within the structure. For example, the applique strips 302-307 may be applied to the structure 204. As another example, the chromatic witness particles 412, 414, 416, 417 may be applied to the structure 204.

The method 700 may further include applying a second material to a second portion of the structure, at 704. The second material may be adapted to change to a second color, distinct from the first color, in response to heating of the second portion of the structure to a second threshold temperature. For example, the applique strips 312-217 may be applied to the structure 204. As another example, the chromatic witness particles 413, 415 may be applied to the structure 204.

Although various embodiments have been shown and described, the present disclosure is not so limited and will be understood to include all such modifications and variations are would be apparent to one skilled in the art.

What is claimed is:

1. A method comprising:
   changing a first material applied to a first portion of a structure to a first color in response to heating of the first portion of the structure to a first threshold temperature due to an electrical current within the structure;
   changing a second material applied to a second portion of the structure to a second color distinct from the first color in response to heating of the second portion of the structure to a second threshold temperature greater than the first threshold temperature; and
   detecting a pathway of the electrical current through the structure based on a position of the first color.

2. The method of claim 1, further comprising:
   estimating, based at least on the first color and the second color, an extent of damage produced by the electrical current along the detected pathway of the electrical current through the structure.

3. The method of claim 1, further comprising:
   successively changing additional materials applied to additional portions of the structure to additional colors distinct from the first color and distinct from each other in response to heating of the additional portions of the structure to additional successively increasing threshold.

4. The method of claim 3, further comprising:
   estimating, based at least on the first color, the second color, and the additional colors, an extent of damage produced by the electrical current along the detected pathway of the electrical current through the structure.

5. The method of claim 1, further comprising:
   scanning a surface of the structure with a detector;
   receiving, at the detector, light from the structure; and
   locating the position of the first color based on the light from the structure.

6. The method of claim 5, further comprising:
   directing a light source at the structure during the scanning, wherein the light source is an ultraviolet light source, and wherein the first color is substantially invisible under non-ultraviolet light.

7. The method of claim 1, wherein the first threshold temperature is between 200° C. and 300° C.

8. The method of claim 1, wherein the first portion of the structure is adjacent to a first applique strip that incorporates the first material, and wherein the second portion of the structure is adjacent to a second applique strip that incorporates the second material.

9. A system comprising:
   a structure;
   a first material applied to a first portion of the structure, the first material adapted to change to a first color locally in response to localized heating of the first portion of the structure to a first threshold temperature due to an electrical current within the structure;
   a second material applied to a second portion of the structure, the second material adapted to change to a second color, distinct from the first color, in response to heating of the second portion of the structure to a second threshold temperature greater than the first threshold temperature; and
   a detector configured to receive light from the structure to enable detection of a pathway of the electrical current through the structure based on a position of the first color.

10. The system of claim 9, wherein the first color enables estimating an extent of damage produced by the electrical current along the pathway of the electrical current through the structure.

11. The system of claim 9, further comprising:
    additional materials applied to additional portions of the structure, the additional materials adapted to change to additional colors, distinct from the first color and distinct from each other, in response to heating of the additional portions of the structure to additional successively increasing threshold temperatures.

12. The system of claim 11, wherein the first color and the additional colors enable estimating an extent of damage produced by the electrical current along the detected pathway of the electrical current through the structure.

13. The system of claim 9, further comprising:
    a light source directed toward the structure, wherein the light source is an ultraviolet light source, and wherein the first color is substantially invisible under non-ultraviolet light.

14. The system of claim 9, wherein the structure includes a copper foil applied to a composite aircraft, a conductive mesh of a composite aircraft, a dielectric top of a composite aircraft, a lightning diversion strip, a grounding cable or plate, a portion of a lightning protection layer of an aircraft, or any combination thereof.

15. The system of claim 9, wherein the first material includes a thermo-chromatic witness material.

16. The system of claim 9, further comprising:
    a first applique strip that incorporates the first material adjacent to the first portion of the structure; and
    a second applique strip that incorporates the second material adjacent to the second portion of the structure.

17. The system of claim 9, further comprising:
    a first set of applique strips that incorporate the first material, at least one applique strip of the first set of applique strips adjacent to the first portion of the structure; and
    a second set of applique strips that incorporate the second material, at least one applique strip of the second set of applique strips adjacent to the second portion of the structure, wherein the first set of applique strips and the second set of applique strips are applied to the structure in a repeating pattern.

18. The system of claim 9, wherein the first material is incorporated into a first portion of a coating matrix and the second material is incorporated into a second portion of the coating matrix, wherein the coating matrix is applied to the structure.

19. The system of claim 9, wherein the first material is incorporated into a first portion of a resin of a lightning protection layer and wherein the second material is incorporated into a second portion of the resin of the lightning protection layer.

20. A method comprising:
changing a first material to a first color in response to heating of a first portion of a structure to a first threshold temperature due to an electrical current within the structure;
changing a second material to a second color distinct from the first color in response to heating of a second portion of the structure to a second threshold temperature greater than the first threshold temperature; and
before changing the first material to the first color and before changing the second material to the second color, applying the first material to the first portion of the structure and applying the second material to the second portion of the structure.

\* \* \* \* \*